(12) United States Patent
Rigaud

(10) Patent No.: US 8,353,217 B2
(45) Date of Patent: Jan. 15, 2013

(54) TEST MACHINE TO APPLY A UNIFORM INTERNAL PRESSURE TO A TUBE

(75) Inventor: Pierre Rigaud, Solerieux (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 177 days.

(21) Appl. No.: 12/993,921

(22) PCT Filed: Aug. 6, 2009

(86) PCT No.: PCT/EP2009/060210
§ 371 (c)(1),
(2), (4) Date: Nov. 22, 2010

(87) PCT Pub. No.: WO2010/015677
PCT Pub. Date: Feb. 11, 2010

(65) Prior Publication Data
US 2011/0259087 A1    Oct. 27, 2011

(30) Foreign Application Priority Data
Aug. 8, 2008 (FR) ...................................... 08 55495

(51) Int. Cl.
*G01B 5/30* (2006.01)
(52) U.S. Cl. ....................................................... 73/760
(58) Field of Classification Search .................... 73/760, 73/798, 834, 49.5
See application file for complete search history.

(56) References Cited

U.S. PATENT DOCUMENTS

| | | | | |
|---|---|---|---|---|
| 3,044,289 | A | * | 7/1962 | Fleischhauer ................ 73/12.01 |
| 3,628,378 | A | * | 12/1971 | Regan, Jr. ....................... 73/798 |
| 3,803,365 | A | | 4/1974 | Cartier |
| 2001/0037687 | A1 | | 11/2001 | Brovold et al. |

FOREIGN PATENT DOCUMENTS

| | | |
|---|---|---|
| FR | 2 087 758 A | 12/1971 |
| GB | 1 478 418 A | 6/1977 |
| WO | 01/33194 A1 | 5/2001 |

OTHER PUBLICATIONS

International Search Report for PCT/EP2009/060210.

* cited by examiner

*Primary Examiner* — Jewel V Thompson
(74) *Attorney, Agent, or Firm* — Pearne & Gordon LLP

(57) ABSTRACT

This machine comprises a central body (1), un piston (3) compressing the liquid contained in a liner (2), and a peripheral bladder (18) capable of uniformly applying pressure to a tube (21) immediately surrounding this bladder. Pressure can be applied in a simple manner through a tensile and compression testing machine (22, 23). No end effect that could disturb the test is produced on the tube.

4 Claims, 2 Drawing Sheets

TEST MACHINE TO APPLY A UNIFORM INTERNAL PRESSURE TO A TUBE

The application of this invention is a test machine designed to apply a uniform internal pressure to a tube in order to perform tests to study a rupture, damage without rupture or creep.

One difficulty with such tests is to apply the pressure without producing any end effects that disturb the results and without hindering axial shrinkage related to Poisson's ratio, observed when a circumferential tension is applied.

Several test methods already exist. One of them can be done with a tensile testing machine. Two parts with a half-disk cross section are placed in the tube at diametrically opposite positions and at a spacing from each other controlled by the machine. Since the rounding of the test parts is identical to the rounding of the tube, they bear on the entire internal face of the tube over their entire width and apply internal pressure due to their contact. This approach is convenient but it has the disadvantage that the pressure resulting from opposing separation forces is not uniform over the circumference of the tube; part of the tube located between them is not subject to any internal pressure and in practice is subject to a bending component in addition to the tension. This introduces an uncertainty on the results and complicates their interpretation. Furthermore, these tests were carried out with small tube heights of the order of only 15 mm, which cannot be representative.

Internal pressures were also applied to tubes by fluid compression by means of pumps. This makes it necessary to close the tube cavity by leak tight clamping of its ends using flanges. But tightening produces axial bending and an end effect due to the constraint at the ends of the tube, and it can also prevent axial shrinkage during the test. It should be added that the use of pumps is not as convenient as a tensile testing machine.

The main objective of the invention was to propose a test method giving precise results by eliminating the end effect and real and complete uniformity of the pressure applied on the tube. An attempt was made to perform this test with a tensile and compression testing machine. We also attempted to make a simple device, enabling fast assemblies and disassemblies to perform tests with large series of samples.

In general, the invention is a test machine to apply a uniform internal pressure to a tube, comprising a body, a piston sliding in the body and varying a volume of a liner machined in the body, an annular elastic bladder surrounding a periphery of the body, the periphery of the body comprising two circular ribs and a recess separating the ribs and communicating with the liner, the machine also comprising two flanges fixed to the body at two opposite ends and comprising annular mating flanges that surround the ribs, the bladder being clamped at each of the two opposite ends between one of the ribs and one of the mating flanges.

Figure 1:
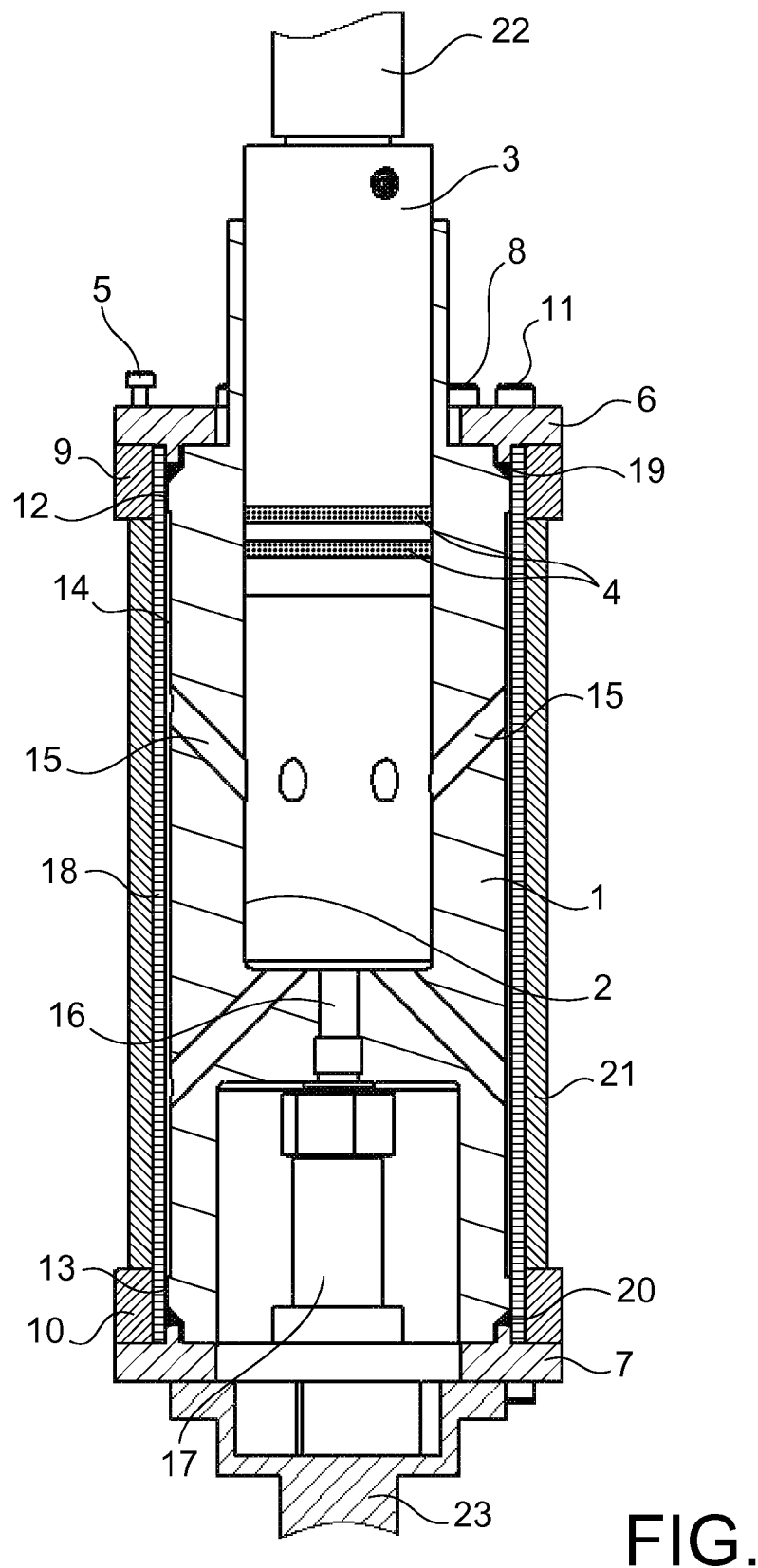
Figure 2:
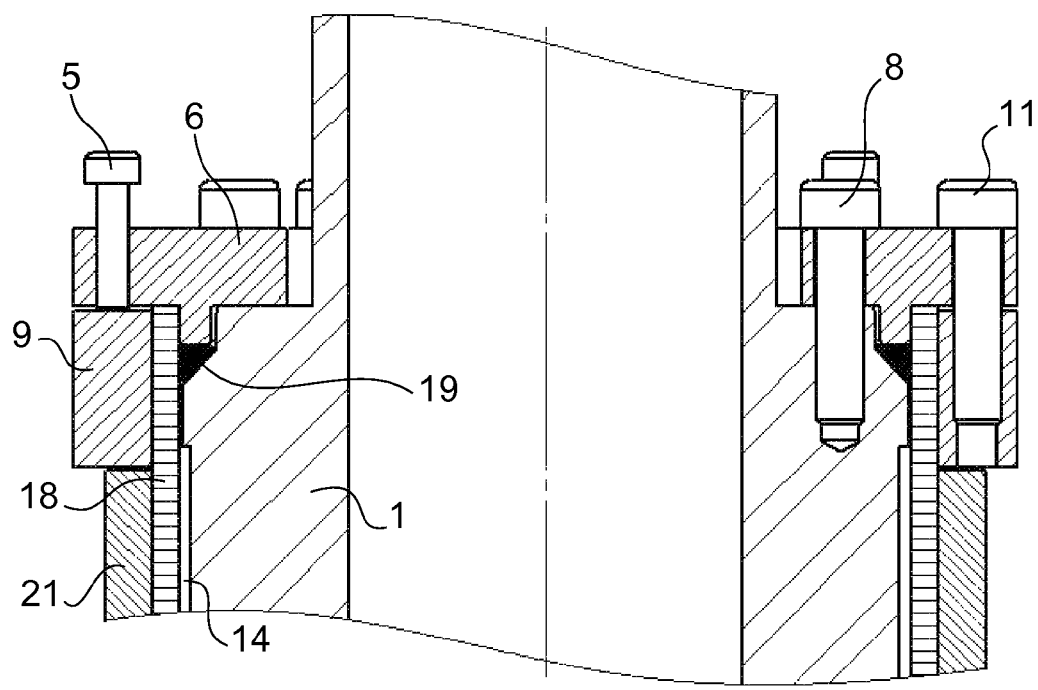

We will now describe the invention with reference to the figures, in which:

FIG. 1 shows a sectional view of the device, and
FIG. 2 shows a manufacturing detail.

The device according to the invention comprises a central cylindrical body 1, inside which a liner 2 that is also cylindrical is machined. A piston 3 slides in the body 1 so as to vary the internal volume of the liner 2. It is provided with seals 4 that provide a dynamic seal with the liner 2 that guides it. The body 1 is provided with two flanges 6 and 7 at its plane and opposite ends, that are fixed to the body 1 by screws 8; mating flanges 9 and 10 are associated with the corresponding flanges 6 and 7 being connected to them by attachment screws 11 and other adjustment screws 5 (FIG. 2). The adjustment screws 5 are threaded in the flanges 6 and 7 and define the distance from the mating flanges 9 and 10 by coming into contact with them; the attachment screws 11 are threaded in the mating flanges 9 and 10 and hold this distance at a fixed value.

The periphery of the body 1 between the plane faces from which the flanges 6 and 7 are made comprises two circular ribs 12 and 13 made facing the mating flanges 9 and 10 and a recess 14 separates the ribs 12 and 13, and communicates with the liner 2 through feed flow streams 15. A special flow stream 16 leads to a pressure sensor 17 made under the body 1.

The machine also comprises an annular shaped elastic bladder 18 arranged around the central body 1. Its ends are held in place between the ribs 12 and 13 and the mating flanges 9 and 10 with small clearances along the direction of the radius of the body 1. Seals 19 and 20 are compressed between the body 1, the bladder 18 and the flanges 6 and 7 beyond the ribs 12 and 13.

When a test is carried out, a tube 21 is arranged around the bladder 18 between the flanges 6 and 7. Liquid is poured into the liner 2, the device is placed between opposite plates 22 and 23 of a tensile and compression testing machine that is not shown in more detail, and the plates 22 and 23 are brought towards each other by applying a determined force on the piston 3 and the flange 7 furthest away from the piston, respectively. The piston 3 is free to move along the axis of the tube 21 and the body 1, and passes through the other flange 6. One of them bears on the piston 3 and the other supports the body 1. The compression force increases the pressure of the liquid in the liner 2 and in the recess 14 by means of the communication provided by the flow streams 15. The result is expansion of the bladder 18 at uniform pressure, and the elasticity of the bladder 18 is such that the pressure is uniformly transmitted to the tube 21. Liquid leaks outside the recess 14 are stopped by seals 19 and 20 located behind the internal face of the bladder 18.

FIG. 2 shows a construction detail. Axial shrinkage of the tube 21 may show up axial clearance between the tube and the mating flanges 9 and 10, which can facilitate extrusion of the bladder 18. It is then proposed to release the attachment screws 11 and then to adjust the adjustment screws 5 to push the mating flanges 9 and 10 back slightly until they come into contact with the tube 21, but without applying any axial force on it.

The invention was used to test 100 mm diameter and 200 mm high tubes at pressures of up to 200 bars. When one tube 21 had been tested, it was replaced by another tube, moving the plates 22 and 23 of the machine apart, disassembling the screws 8 to remove the flanges 6 and 7 and then performing the operations in the reverse order. This is done very quickly.

The invention claimed is:

1. Test machine to apply a uniform internal pressure to a tube (21), comprising a body (1), a piston (3) sliding in the body and varying a volume of a liner (2) contained in the body (1), an annular elastic bladder (18) surrounding a periphery of the body, the periphery of the body comprising two circular ribs (12, 13) and a recess (14) separating the ribs and communicating with the liner (2), the machine also comprising two flanges (6, 7) fixed to the body at two opposite ends and comprising annular mating flanges (9, 10) surrounding the ribs (12, 13) respectively, the bladder (18) being clamped at each of the two opposite ends between one of the ribs and one of the mating flanges.

2. Test machine according to claim 1, characterised in that mating flanges are fixed to flanges through means (11, 5) for adjusting the distance between mating flanges.

3. Test machine according to claim 2, characterised in that means (11, 5) for adjusting the distance between mating flanges comprise attachment screws and distance adjustment screws.

4. Test machine according to any one of claims 1 to 3, characterised in that it is associated with a tensile and compression testing machine, on plates (22, 23) of which the piston (3) and one of the flanges (7) are installed respectively.

* * * * *